United States Patent
Raspopin et al.

(10) Patent No.: US 7,170,085 B2
(45) Date of Patent: Jan. 30, 2007

(54) FREQUENCY SELECTIVE TERAHERTZ RADIATION DETECTOR

(75) Inventors: Alexander S. Raspopin, Jersey City, NJ (US); Hong-Liang Cui, Jersey City, NJ (US)

(73) Assignee: Stevens Institute of Technology, Hoboken, NJ (US)

( * ) Notice: Subject to any disclaimer, the term of this patent is extended or adjusted under 35 U.S.C. 154(b) by 212 days.

(21) Appl. No.: 10/919,568

(22) Filed: Aug. 17, 2004

(65) Prior Publication Data

US 2005/0093023 A1    May 5, 2005

Related U.S. Application Data

(60) Provisional application No. 60/495,968, filed on Aug. 18, 2003.

(51) Int. Cl.
*H01L 29/06* (2006.01)
*H01L 29/739* (2006.01)
*H01L 27/10* (2006.01)

(52) U.S. Cl. .................. 257/21; 257/194; 257/202

(58) Field of Classification Search ............ 257/21, 257/194, 202
See application file for complete search history.

(56) References Cited

U.S. PATENT DOCUMENTS

| 5,729,017 A | * | 3/1998 | Brener et al. ............ 250/338.1 |
| 5,894,125 A | | 4/1999 | Brener et al. ............... 250/330 |
| 5,914,497 A | * | 6/1999 | Sherwin ..................... 257/21 |
| 6,479,822 B1 | * | 11/2002 | Nelson et al. ........... 250/341.1 |

OTHER PUBLICATIONS

E.Schomburg; F. Klappenberger, M. Kratschmer, A.A. Ignatov, K.F.Renk and W. Wegscheider Ultrafas, ultra-broadband superlattice detector for THz radiation Thz conference 2000, Darmstadt, Germany Sep. 28-29, 2000( 2000) 91-93.*
S. Winnert "GaAs/ALAs superlattice for detection of terahertz radiation" Microelectronics Journalvol. 31 ( 2000) pp. 389-396.*

* cited by examiner

*Primary Examiner*—Long Pham
*Assistant Examiner*—Shrinivas H. Rao
(74) *Attorney, Agent, or Firm*—Licata & Tyrrell P.C.

(57) ABSTRACT

The present invention provides a device for frequency-selective detection of electromagnetic radiation in the terahertz region of the electromagnetic spectrum using a lateral semiconductor superlattice, a metal antenna attached to the lateral semiconductor superlattice; and a resonator comprising two mirrors and a substrate. A method for detecting electromagnetic radiation using the device is also provided.

1 Claim, 8 Drawing Sheets

Superlattice based dc detector.

Electron climbing the Wannier-Stark ladder.
Detection mechanism

The equivalent transmission line for the THz-photon detector based on layered superlattice.

FREQUENCY SELECTIVE TERAHERTZ RADIATION DETECTOR

INTRODUCTION

This application claims the benefit of U.S. Provisional Application No. 60/495,968, filed Aug. 18, 2003.

BACKGROUND OF THE INVENTION

Terahertz (THz) electromagnetic radiation has recently found increasing prominence in various fields of science and technology, including identification of biological microspecies, communications for which an increase of several orders of magnitude in bandwidth (as compared with current wireless technology) is required, and identification of metal objects of millimeter size. One of the major obstacles preventing widespread applications of terahertz technology is the lack of powerful tunable sources and sensitive detectors in this frequency regime of the electromagnetic spectrum.

U.S. Pat. No. 5,914,497 discloses an electromagnetic wave detector made of a semiconductor material with a quantum well structure. Detection is based on the effect of changing resistance of electron transport through quantum wells due to absorption of THz photons between two levels of quantum wells, due to the electron population inversion. The detector requires cooling to temperatures of about ten degrees Kelvin.

U.S. Pat. No. 5,729,017 discloses a device which uses electric field interaction with optical beams in biased metal semiconductor microstructures.

U.S. Pat. No. 5,894,125 uses femtosecond pulse laser for excitation of THz radiation.

The present invention provides a novel radiation detector in the terahertz region of the electromagnetic spectrum.

DESCRIPTION OF THE INVENTION

Figure 1:
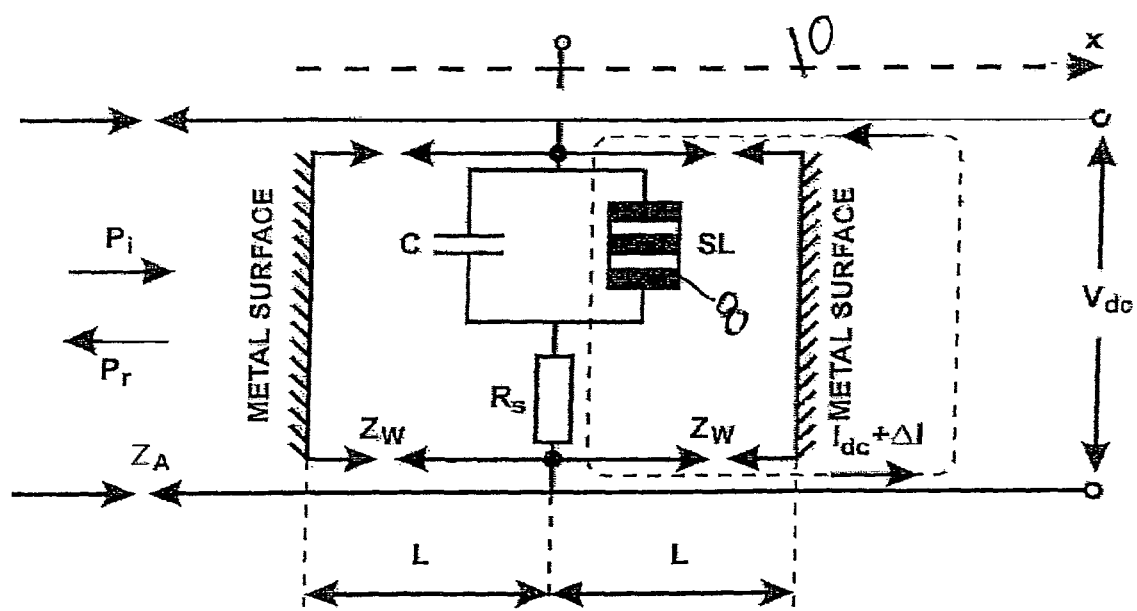
FIG. 1 shows a circuit for a THz-photon resonator detector.

The present invention relates to a frequency selective Terahertz detector based on a semiconductor superlattice with a resonator. The invention provides a photon resonant detector (resonator) using a semiconductor superlattice technology for a proper detection. The resonator is installed to a selected frequency and the enhanced amplitude of the internal electric field in the semiconductor superlattice and responsivity at the selected frequency is observed based on the standing wave principle. The present device employs Molecular Beam Epitaxy (MBE)[or Metallo-organic Chemical Vapor Deposition (MOCVD)] growth of the lateral semiconductor superlattice; metal deposition, and photolithography. Depending upon the characteristics of the materials, the operating frequency ranges between 0.5 THz to 25 THz, if the effective electron scattering frequency in lateral superlattice is 0.5 THz and the superlattice miniband width is 0.1 eV. High quality semiconductor superlattices are made by using Molecular Beam Epitaxy (MBE) technology, their effective electron scattering frequency can achieve very low values at room temperature where the $f_{scattering}$ value is about 0.05 THz. This value sets the lower limit for detection. The upper limit for detection is determined by the width of the superlattice miniband divided by Plank's constant, permitting detection for example, in the 0.05 to 25 THz range if the superlattice miniband width is 0.1 eV. The frequency-selective detector of the present invention operates at room temperature, and uses standing wave enhancement of the detector responsivity. The detector contains a lateral semiconductor superlattice with electrons performing Bloch oscillations as an active medium, a broadband bow-tie terahertz (THz) antenna, a built-in resonator and an external dc circuit. The lateral (surface) superlattice is a superlattice where an additional potential is produced for two dimensional electrons localized near a surface of semiconductor substrate. It can be the one-dimensional chains of identically coupled GaAs/GaAlAs quantum dots—a form of quantum wires, sometimes called quantum boxes, or quantum dots (GaAs) imbedded in a thin epilayer of GaAlAs. The lateral superlattices are grown by means of Molecular Beam Epitaxy (MBE) and also by Metalorganic Chemical Vapor Deposition (MOCVD). Furthermore, the lateral superlattice can be successfully overgrown with upper substrate. The lateral superlattice is not necessarily a thin superlattice. At present, there has been a technological advance culminating in the growth of three-dimensional cluster lattice, which is actually a range of lateral superlattices grown one on another. The lateral superlattice leads to a necessary change in technology of antenna attachment to the superlattice and allows the additional growth of a resonator. The estimation calculations of the current responsivity of the proposed detector fulfilled by means of an equivalent transmission line model have showed that the detector responsivity can be enhanced in several hundred times near a resonance frequency due to the matching between the incident radiation and the superlattice provided by built-in resonator. The expected rise time of the proposed detector is in order of $10^{(-11)}$ s.

Figure 2:
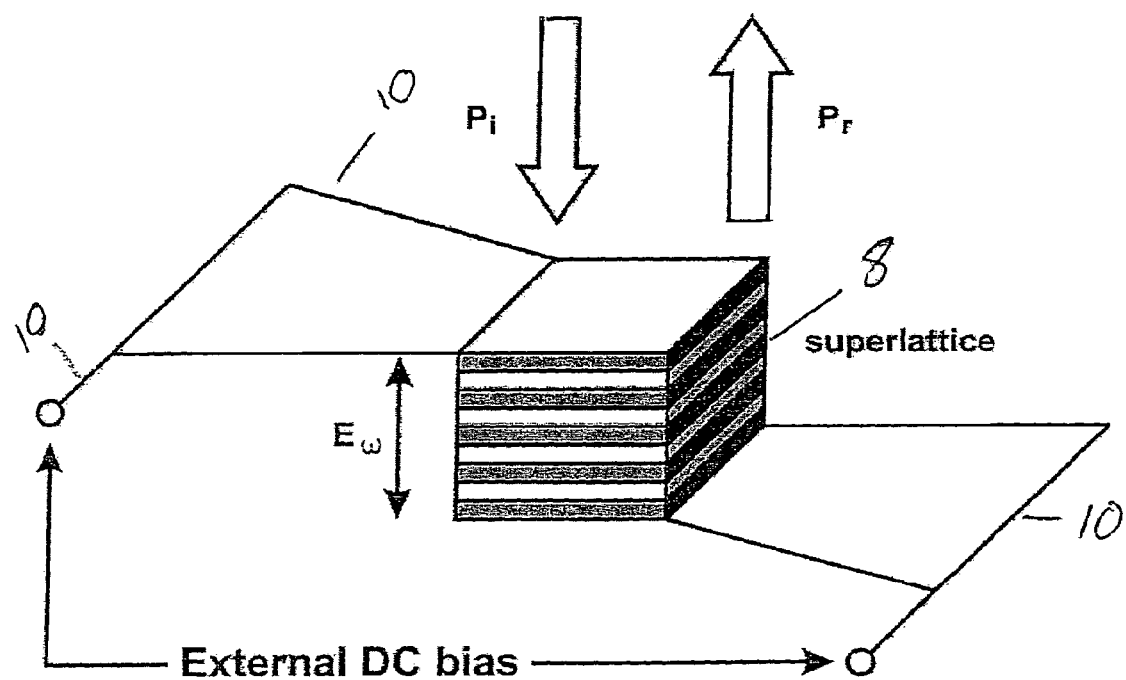
FIG. 2 shows a THz-photon detector coupled to an N-period planar semiconductor superlattice with a co-planar broadband bow-tie THz metal antenna. The THz-photon detector is based on layered superlattice. The superlattice is comprised, for instance, of GaAs, Al(In)GaAs layers.
Figure 3:
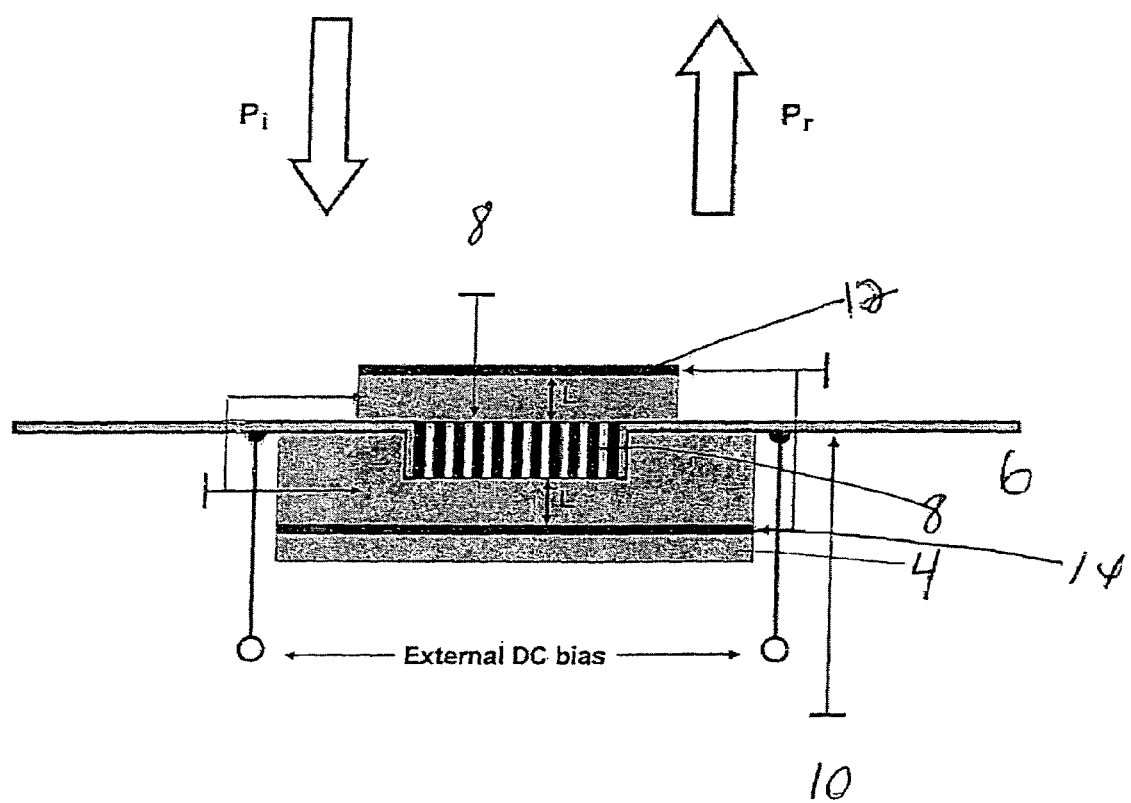
FIG. 3 shows a projection view of the THz radiation detector based on a lateral semiconductor superlattice and resonator.
Figure 5:
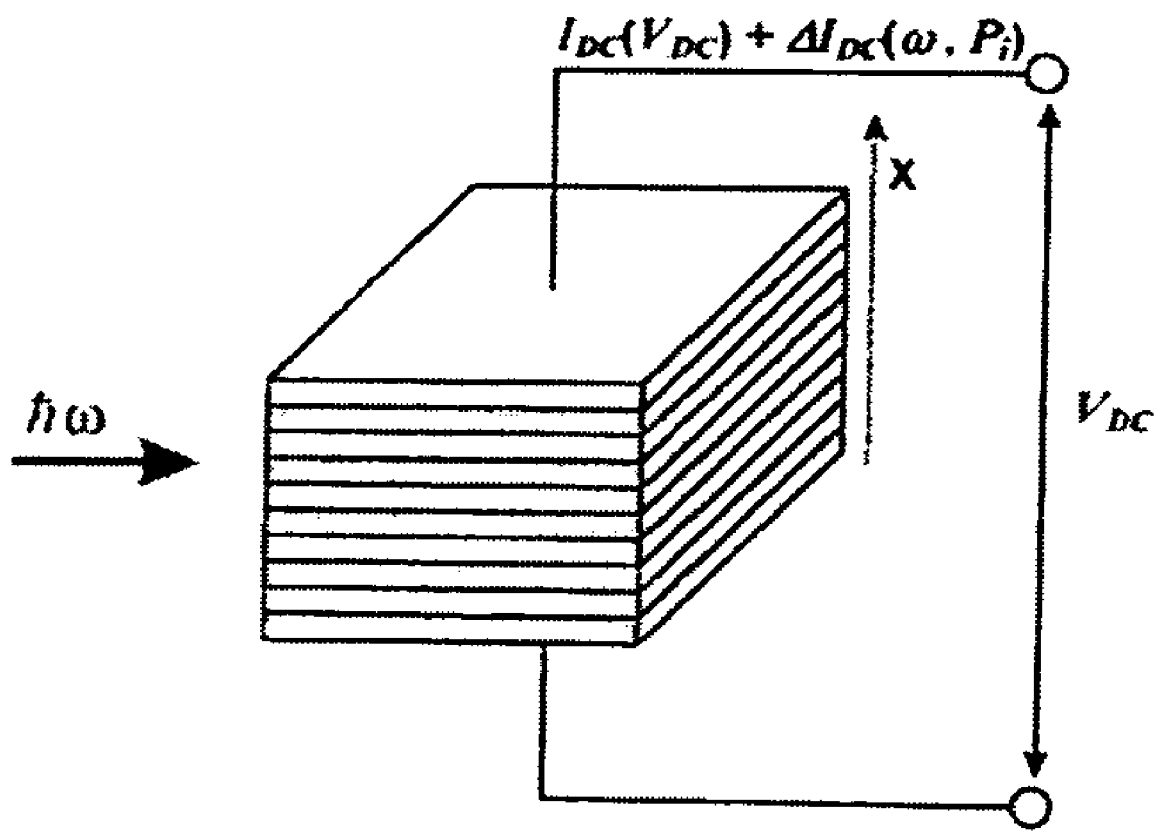
FIG. 5 shows one priniple of the superlattice based dc detector.

Terahertz electromagnetic radiation is useful for identification of biological micro species, communications, in which several orders of magnitude of increase in bandwidth as compared with current wireless technology is expected, and in detection, in which it is capable of identifying metal objects of millimeter size and hidden from view. One of the major obstacles preventing widespread applications of terahertz technology is the lack of powerful, tunable sources, and sensitive detectors in this frequency regime of the electromagnetic spectrum. The present invention provides a sensitive THz detector, which exploits the extremely strong nonlinear dispersion relation for the electrons in the limit of a single miniband of a semiconductor superlattice. The THz ray passes through compositions such as cloth, paper, and polymers to allow for detection of mettalics, ceramics, plastics, and identification of explosives by their characteristic spectral fingerprints. With the technology of the present invention detection of concealed plastic weapons such as knives or guns would be possible. Designs of this detector are shown in FIGS. 2 and 3. FIG. 5 shows a principal design of THz-photon detector based on semiconductor superlattice. THz radiation is coupled to an N-period semiconductor superlattice by a coplanar broadband bowtie antenna, wherein $P_i$ and $P_r$ are the incident and reflected powers, respectively. The equivalent transmission line for this THz-photon detector with a dc bias voltage source is shown in the FIG. 7, where SL—superlattice (miniband electrons capable to perform-Bloch oscillations), C—superlattice capacitance, $R_s$—parasitic high-frequency resistance, $Z_A$—bowtie antenna impedance, $V_{dc}$—dc bias voltage, $\Delta I_{dc}$—induced dc current change. This equivalent circuit allows treatment of the high-frequency response of the miniband electrons and, simultaneously, take into account a finite matching efficiency between the detector antenna and the superlattice in the presence of parasitic losses. The data from experiments 8–10 with THz detectors based on one-dimensional layered semiconductor superlattice has proven the adequacy of this equivalent transmission line model.

The current development of THz-photon detector with a quantum superlattice has concentrated on exploiting the one-dimensional layered superlattice as an active medium. The use of a lateral quantum semiconductor superlattice as an active medium instead of a layered superlattice has not been considered prior to the present invention. The present invention leads to a necessary change of the broadband antenna technology attachment to the superlattice and, more importantly, to the design of a resonant detector with frequency-selective properties.

The device of the present invention is a frequency selective terahertz radiation detector in the terahertz region of the electromagnetic spectrum. Frequency-selective detection is able to be used for microwave, THz (terahertz) and far-infrared band of the electromagnetic spectrum.

The device comprises a lateral semiconductor superlattice (FIG. 3 or 8) (8), a metal antenna (10); a resonator (20); and a substrate (4). The metal antenna (10) is attached to the lateral semiconductor superlattice (8). The resonator (20) is formed by a first metal mirror (2) and a second metal mirror (14) with a substrate (4) fill. The substrate (4) may also form insulating layers of the resonator (20). The metal antenna (10) connects the lateral semiconductor superlattice (8) (preferably through Ohmic contacts, FIG. 8) to an external circuit with DC bias voltage source and allows DC current to flow through the lateral semiconductor superlattice (8) so that the effect of incident radiation absorption within one miniband in the lateral semiconductor superlattice (8) induces additional DC current flowing in an external circuit which can be readily detected. The metal mirror may comprise materials such as bulk metal mirror, metal powder mirror, and n+(n++) doped semiconductor layer, the quality of the detection will be different depending on the chosen medium. Metal mirror as a bulk medium has some drawbacks such as cost and usually bulk metal is changed to metal powder, further the bulk medium and metal powder have lesser quality as a mirror than a mirror comprised of n+(n++) doped semiconductor layer. In addition, photonic crystal (the appropriate photonic crystal in the appropriate electromagnetic band) can be used to make the mirrors of the present invention. The present invention may be configured into many possible configurations using similar components.

FIG. 1 shows an elevational view of the circuit for the THz photon resonant frequency selective terahertz radiation detector mounted to a metal antenna. The metal antenna is a broadband-THz receiving antenna, which is preferably shaped into a bowtie configuration. In the case of Terahertz radiation when the radiation frequency matches the frequency of the resonant absorption, the electrons in the active region present a purely resistive load on metal antenna. THz radiation absorption within one miniband of the lateral semiconductor superlattice (8) induces an additional DC current flowing in an external circuit which can be readily detected. For maximum responsivity, if the frequency of the incident wave is equal to some characteristic frequency close to the resonant frequency of the oscillatory circuit, the reactive part of the impedance of that load tends to zero. At such a frequency the maximum possible power of incident radiation will be absorbed and the responsivity will be substantially increased. This is one of the main advantages of the present resonant frequency-selective terahertz radiation detector based upon a lateral semiconductor superlattice (8).

FIG. 1 demonstrates an equivalent circuit for a THz-photon resonator detector with a DC voltage bias source. In FIG. 1, $Z_A$ represents the wave impedance of the receiving (bowtie shaped) metal antenna; $Z_W$ represents the wave impedance of insulating resonator infill with length 2L; $R_S$ represents the parasitic high frequency losses, C represents the parasitic superlattice capacity, SL represents the semiconductor superlattice; $P_i$ and $P_r$, represent the incident ($P_i$) and reflected ($P_r$) THz radiation power on the frequency selective terahertz radiation detector and reflected by the detector; $V_{DC}$ represents the external DC voltage bias applied to lateral semiconductor superlattice (8); $I_{DC}+\Delta I$ represents the DC current flowing in an external circuit through the lateral semiconductor superlattice (8).

As shown in FIGS. 2 and 3, the semiconductor superlattice (8) may comprise layers such as GaAs, and AL(In)GaAs. There is no restriction on components which may be used in the layers but the whole grown semiconductor nanostructure must show a quantum superlattice property, namely appearance of a miniband in the energy spectrum.

Figure 8:
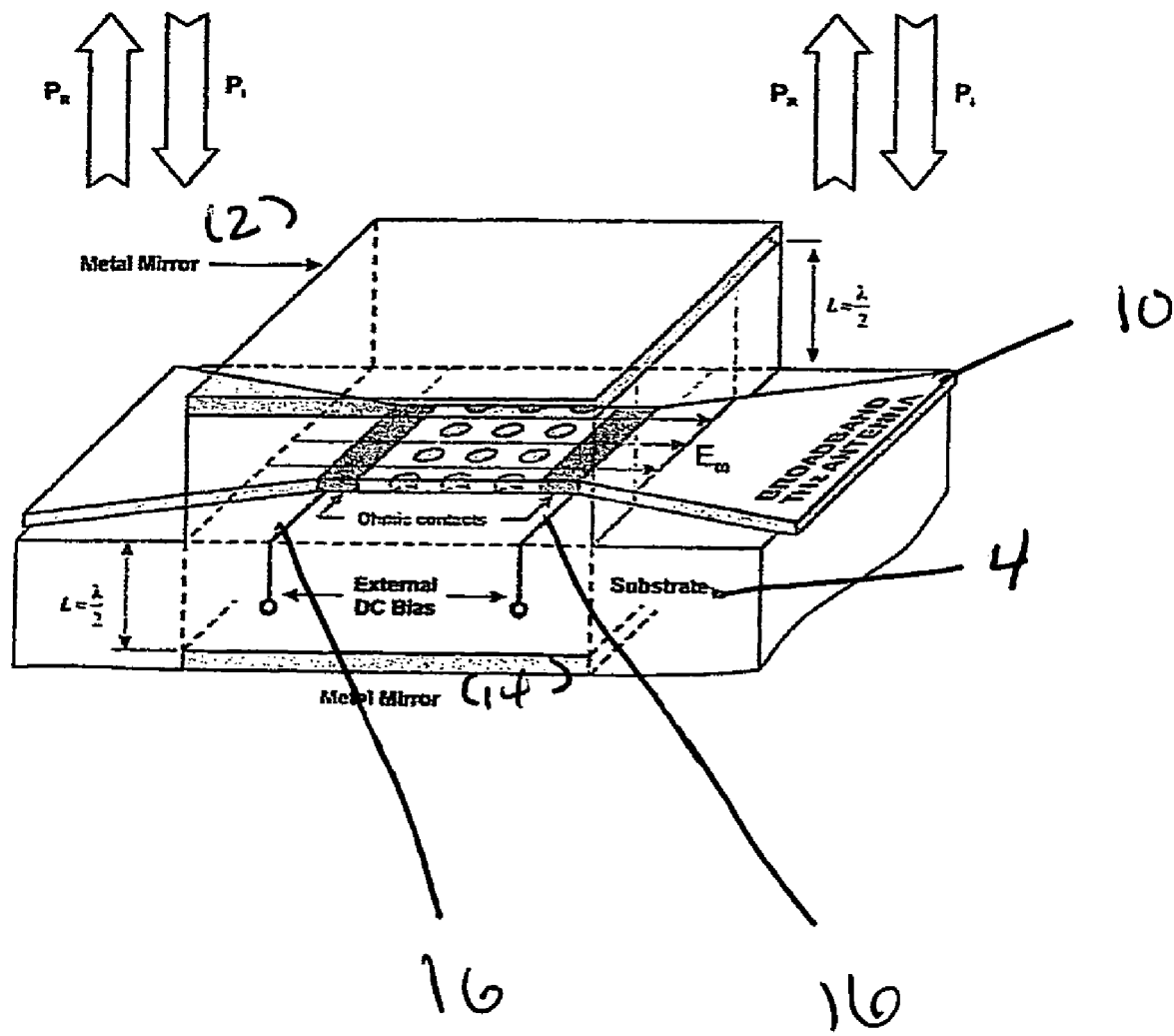
FIG. 8 shows a possible three dimensional design of the present frequency-selective detector based on lateral (surface) semiconductor superlattice.

The frequency selective terahertz radiation detector device, as depicted in FIGS. 3 and 8, comprises a first metal mirror (2); a substrate (4), a first insulating layer (6); a lateral semiconductor superlattice (8); a metal antenna (10); a second insulating layer (12); a second metal mirror (14) and at least two wires (16) which are connected to the metal antenna (10). The first metal mirror (2) is grown or deposited upon the main substrate. The first insulating layer (6), may be comprised of substrate, such as GaAs, with determined width L. The first insulating layer (6) is grown on the first metal mirror (2). The lateral semiconductor superlattice (8) is grown on the first insulating layer (6); a metal antenna (10)(such as a bow-tie THz receiving antenna) is grown on the first insulating layer (6) and attached to the lateral semiconductor superlattice (8). The second insulating layer (12) may be comprised of GaAs, or any other suitable material. The second insulating layer (12) with determined width L is grown on the plane of a lateral semiconductor GaAs/Al(In)GaAs superlattice and metal antenna. The second metal mirror (14) is grown on the second insulating layer (12). Two metal wires (16) are connected to the metal antenna (10) at any two antenna points (preferably by Ohmic contacts) to connect the Frequency Selective Terahertz detector device to the external circuit with DC bias voltage source and to provide DC current flowing through lateral semiconductor superlattice (8). The first metal wire (16) is connected to the first Ohmic contact so that it is attached to the first GaAs(Al(In)GaAs) layer of the lateral semiconductor superlattice (8). The second metal wire (16) is connected to the second Ohmic contact which is attached to the last GaAs(Al(In)GaAs) layer of the lateral semiconductor superlattice (8).

In a preferred embodiment, the frequency selective terahertz radiation detector is comprised of a main substrate, a first insulating semiconductor layer and a second insulating semiconductor layer, a GaAs/Al(In)GaAs lateral superlattice (or one made from other semiconductors), a metal antenna, a resonator formed by a first mirror and a second mirror and an external DC voltage bias source. The two insulating layers serve as resonator infill. The design allows polarization of exited current to be parallel to the metal mirrors which then leads to effective pumping of THz resonator. The mirrors are preferably metal. The metal antenna is a broadband THz receiving antenna. The metal antenna may be bowtie shaped and is used for the injection of the THz radiation to the lateral semiconductor superlattice (8). The metal antenna comprises two metal triangle (preferably, or any other) planes that are mounted to the first and the last lateral semiconductor superlattice (8) layers directly or through ohmic contacts. In a preferred embodiment, the lateral semiconductor superlattice (8) is comprised of a quantum superlattice which is grown on a semi-insulating layer (substrate) of GaAs as periodic-layers of a GaAs and Al(In)GaAs doped with donor semiconductor, for example Si, up to the electron concentration $N_e \sim 10^{16}$–$10^{18}$ cm$^{-3}$. The high doped case is strongly preferable. The external DC bias source may comprise any suitable DC voltage source and must provide the internal DC electric field ($E \sim E_p$) in lateral semiconductor superlattice (8) for better detection efficiency.

FIG. 8 shows that the electric field is parallel to the plane of the metal antenna and lateral semiconductor superlattice (8) axis which is perpendicular to GaAs/Al(In)GaAs superlattice layers. The metal antenna is attached to the active medium, namely the lateral semiconductor superlattice (8). A first metal mirror (2) and a second metal mirror (14) are parallel to the plane of the bow-tie metal antenna and lateral semiconductor superlattice (8) axis. The whole device represents a resonant structure with possible effective resonant absorption of the incident radiation power. The latter is only possible for a lateral superlattice, and can not be achieved by using planar superlattice as is depicted by the embodiment shown in FIG. 2. The frequency selective terahertz radiation detector is based on the effect of the incident radiation absorption within one miniband in the superlattice which induces additional DC current flowing in an external circuit. The additional DC current can be readily detected. No cooling is required for use of the detector. The frequency selective terahertz radiation detector of the present invention can operate at room temperature and detect with enhanced responsivity near resonance frequencies which are the multiple frequencies of the lowest resonant frequency. The frequency selective terahertz radiation detector of the present invention is a resonant structure which is adjusted for a concrete frequency, being any frequency from 0.5 THz up to 25 THz in the case of semiconductor superlattice with the superlattice miniband width 0.1 eV. A metal antenna can be matched for concrete frequency. The quality of the detection near the chosen concrete frequency is expected to be (f/Δf) or about 500, which is far superior to the traditional THz detectors without resonators, which are based on interband electron transport at room temperature.

The presence of the resonator (20) in the circuit of the frequency selective terahertz radiation detector generates a series of the transversal modes of frequencies given by $f_{res}=n\,(c/2L)$, where L is the resonator length (the length of each GaAs insulating layers), c is the speed of the electromagnetic wave in resonator infill and n is an integer number. The frequency selective terahertz radiation detector absorbs radiation resonantly near these frequencies. The resonator (20) can be set or locked to desired resonance frequencies. The resonator (20) of the present invention performs the dual duties of incident power cumulation as well as frequency filtering. For operation in a wider frequency range an array of such detectors with different lengths of resonators can be used. Thus, high responsivity in the whole frequency range will be assured.

FIG. 5 shows a superlattice based dc detector.

Figure 7:
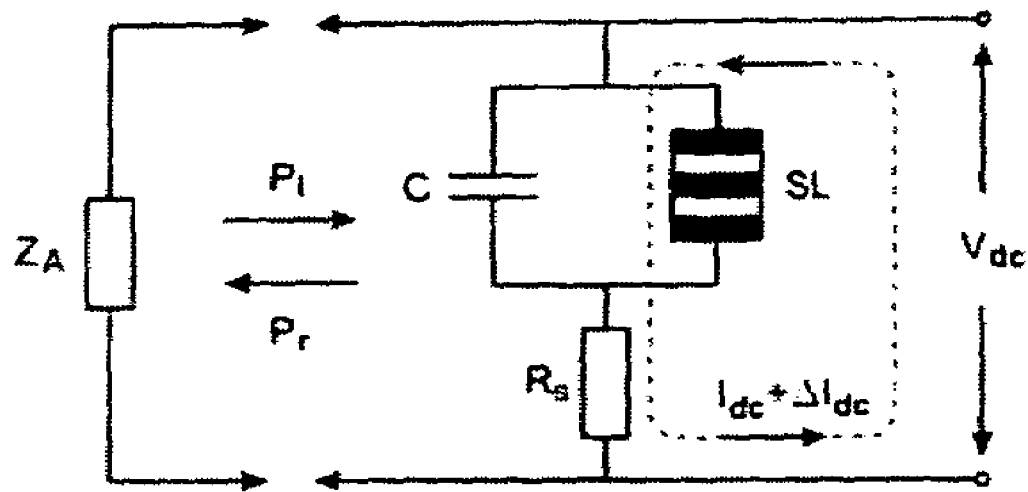
FIG. 7 shows the equivalent transmission line for the THz photon detector based on layered superlattice.

FIG. 7 shows the transmission line for the frequency selective THz photon detector based on a lateral superlattice with a built in resonator (for example as depicted in FIG. 8).

As shown in FIG. 8, the resonant design of the device is capable of detection outside of Terahertz ranges. The frequency selective terahertz radiation detector device, as depicted in FIG. 8, comprises a first metal mirror (2); a substrate (4); a metal antenna (10); a second metal mirror (14) and at least two wires (16) which are connected to the metal antenna (10). Two metal wires (16) are connected to the Ohmic contacts or to the metal antenna (10) at any two antenna points to connect the Frequency Selective Terahertz detector device to the external circuit with DC bias voltage source and to provide DC current flowing through the lateral surface of the device. Any active material in the corresponding microwave or terahertz ranges can be used or applied as long as the medium has a lateral surface.

Figure 6:
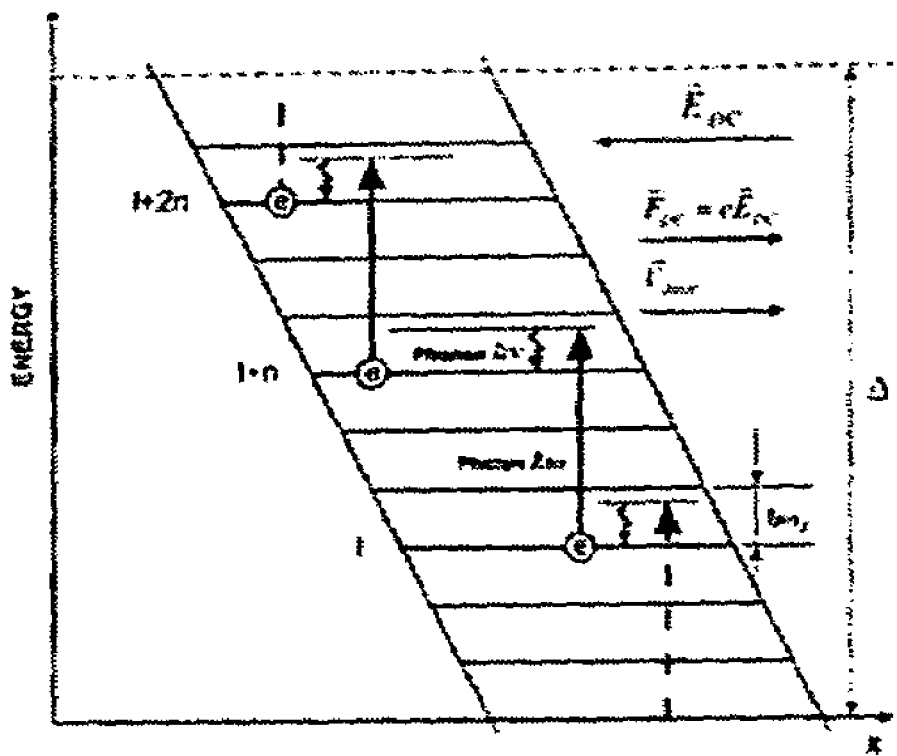
FIG. 6 shows an electron climbing the Wannier-Stark ladder detection mechanism.

The device of the present invention requires a voltage source such an external circuit to apply DC bias to the superlattice and to measure the photocurrent being induced by the incident radiation. FIG. 6 shows an electron climbing the Wannier-Stark ladder detection mechanism.

The basic principle of operation of the frequency selective terahertz radiation detector is the use of the exploitation of an extremely strong nonlinear dispersion relation for the electrons in the limit of a single miniband of a lateral semiconductor superlattice. For instance, in response to an incident radiation of the THz frequency, the device of the present invention induces a constant (DC) voltage/current, in addition to the Esaki-Tsu voltage-current characteristics. This additional current ΔI, being induced by the incident radiation, can be registered by an external circuit as a measure of the power of the incident THz radiation. At selected frequencies, the claimed frequency selective terahertz radiation detector device induces maximum DC current at the same spectral density of incident radiation. This effect is not provided by the previous THz detectors.

High quality semiconductor superlattices are made by using Molecular Beam Epitaxy (MBE) technology, their effective electron scattering frequency can achieve very low values at room temperature where the $f_{scattering}$ value is about 0.05 THz. This value sets the lower limit for detection. The upper limit for detection is determined by the width of the superlattice miniband divided by Plank's constant, permitting detection for example, in the 0.05 to 25 THz range if the superlattice miniband width is 0.1 eV.

The most important characteristic of any detector is its responsivity. The frequency selective terahertz radiation detector responsivity is defined as the induced current (ΔI), divided by the incident wave power. The responsivity of the superlattice frequency selective terahertz radiation detector strongly depends upon frequency. The typical values for the responsivity of traditional detectors based on planar superlattice are 0.01 to 0.05 A/W at 6.0 THz. The reason for such low responsivity is that the geometry of the traditional detector does not allow for a maximum signal induced by incident radiation, because the reactive part of the impedance of the superlattice is uncompensated, leading to an unmatched input impedance with the effective load impedance. As a result, there is a dispersion of the power of the incident radiation at high frequencies because $R_{active}$ is much less than $R_{reactive}$. At high frequencies, and with a high concentration of electrons in the superlattice miniband, this structure becomes a plasma layer which reflects almost all the incident radiation and absorbs very little of it. The responsivity depends only on the absorbed part of the incident radiation which is proportional to the active part of the impedance. The reactive part of the impedance can be efficiently decreased by introducing a resonator to the equivalent circuit of the frequency selective terahertz radiation detector, resulting in a transmission line with a resonance frequency. Thus, the responsivity can be increased by decreasing the reactive part of the impedance of the lateral semiconductor superlattice.

Figure 4:
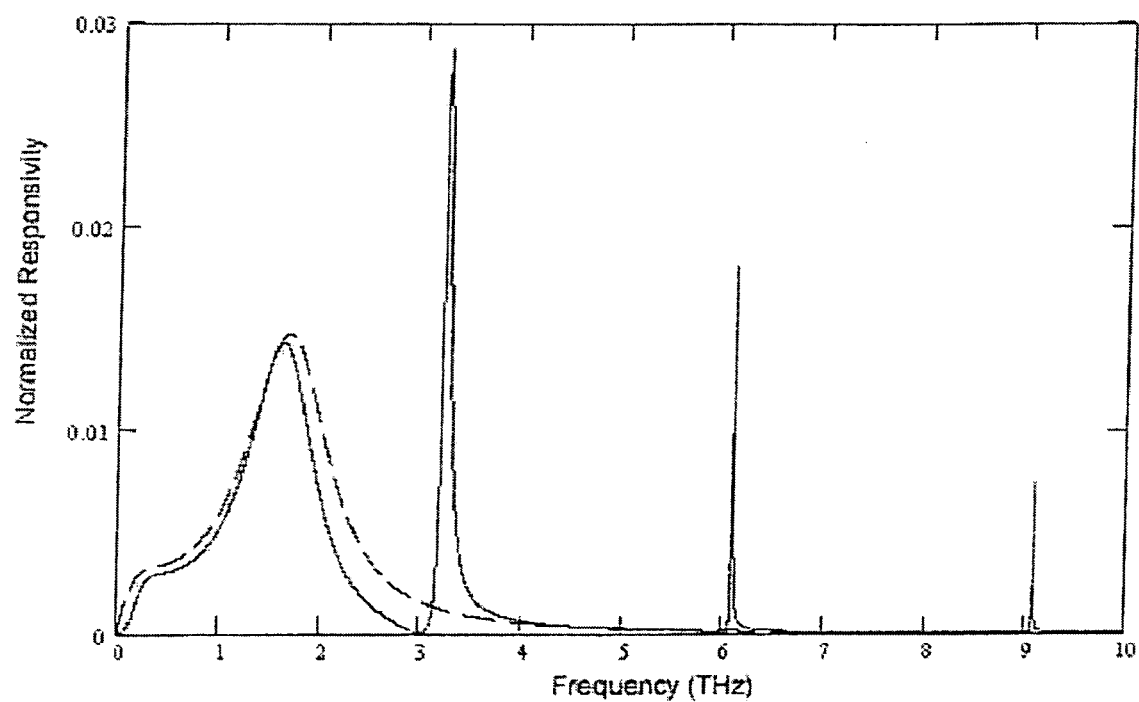
FIG. 4 shows the frequency dependence of normalized responsivity of a frequency selective THz detector as compared with a traditional THz detector.

Numerical simulations of the THz-photon resonant detector in detection of THz radiation have been performed. Characteristic theoretical dependence of normalized responsivity, (responsivity divided by the quantum efficiency e/hf) on frequency of incident radiation is shown, in FIG. 4, where the solid line represents the normalized responsivity dependence of the claimed frequency selective terahertz detector with typical superlattice parameters. The dashed line, shows the normalized responsivity dependence of the existing terahertz detector based on a planar superlattice with the same superlattice parameters. The superlattice period is d=5 nm, length $L_{SL}$=0.5 micron, mesa radius a=3.0 micron, maximum current density is $j_p$=100 kA/cm², relaxation frequency is $f_v$=0.5 THz, normalized applied bias $E/E_p$=0.7, where $E_p$=4 kV/cm is electric field corresponding to the maximum current density, resonance frequency is $f_0$=3.0 THz. The frequency selection quality at f=6.05 THz is $\Delta f/f$=1.7×10⁻³ and responsivity R(6.05 THz)=0.72 A/W, which is about 150 times better than of existing detectors, which typically have $R_{existent}$(6.05 THz)=0.005 A/W. There are no limitations as to thickness of the layers, size, number of layers materials, conducting ability restriction for the lateral semiconductor superlattice which is grown as active medium in the claimed detector, but the efficiency of the detection of claimed frequency selective terahertz radiation detector and, in particular, the selective quality property depend on all of these values.

A method of detecting THz electromagnetic radiation using the device of the present invention comprises applying a voltage source to the lateral superlattice through the metal antenna, then inducing additional DC current flowing from the lateral superlattice in an external circuit which can be readily detected and detecting a change in DC current (DC resistance) in the external circuit, so as to generate a signal indicative of detection of THz electromagnetic radiation. The enhanced responsivity of detection near the chosen resonance frequency is adjusted by the length of the resonator infill.

The devices and methods of the present invention are particularly useful in security devices. The devices and methods of the present invention allow for detection of plastic knives, plastic guns, plastic housings or other concealed plastic materials which are undetectable by traditional security devices and methods.

Many alterations and modifications may be made by those having ordinary skill in the art without departing from the spirit and scope of the invention. Therefore, it must be understood that the illustrated embodiment has been set forth only as an example and that it should not be interpreted as limiting to the present invention or its claims.

EXAMPLES

Example 1

Dependence of Frequency

To solve the prediction of the dependence of the frequency selective THz radiation detector on its technical parameters the process of interaction between incident wave and terahertz detector by the use of the equivalent wave-line description is used. The equation for all propagating waves taken at the superlattice position (x=0) is as follows:

$$U_i+U_r=U_{i1}+U_{r1}=U_{i2}+U_{r2}$$

$$U_{i1}e^{ikL}+U_{r1}e^{-ikL}=U_{i2}e^{-ikL}+U_{r2}e^{ikL}=0$$

$$[(U_i-U_r)/Z_A]+[(U_{i1}-U_{r1})/Z_W]-[(U_{i2}-U_{r2})/Z_w]=[(U_i+U_r)/Z_c],$$

where $U_i$, $U_{i1}$, $U_{i2}$, $U_r$, $U_{r1}$ and $U_{r2}$ are voltage amplitudes of the six waves existing in the system. $U_i$ is a voltage in the incident wave upon broadband metal antenna of the detector, this wave is propagating toward x-axis, $U_r$ is a voltage in the wave reflected by the detector; $k=\epsilon^{1/2}/c_0$ is the module of the wave vector in the GaAs-resonator infill. $\epsilon$=12.9 is the dielectric constant for GaAs, $c_0$ is the light velocity in a vacuum; $Z_A$, $Z_W$ are wave impedances of metal antenna and resonator infill, $Z_W$=377/$\epsilon^{1/2}$ (ohm); $Z_C=R_S+1/(G_{AC}+i2\pi fC)$ is the effective impedance at superlattice position; C is the capacitance of the superlattice, $R_S$ is the resistance of the parasitic high frequency losses: $G_{AC}$ is the superlattice ac conductance, f is the frequency of incident THz radiation which is to be detected by claimed frequency-selective terahertz detector.

The first two equations are the boundary conditions at x=0 with metal mirrors; the final equation is the equation for currents. The expression for the responsivity of the frequency-selective THz detector is obtained as follows:

$$R=[2|F_2(2\Delta f,V_{dc})|/Re(1/Z_A)]\cdot|(G_{AC}+i2\Delta fC)^{-1}\bullet[R_S+(G_{AC}+i2\Delta fC)^{-1}]^{-1}\{1+Z_A[R_S+(G_{AC}+i2\Delta fC)^{-1}]^{-1}-(Z_A/Z_w)(2i/\tan(\Delta f/f_0))\}^{-1}|^{2},$$

where f is the frequency of the incident wave, $f_0=c_0/(2\Delta^{1/2}L)$ is the lowest resonance frequency of the system. The expression for responsivity of the existing superlattice detector can be obtained for the above recited equation assuming that $Z_W$=infinity.

Example 2

Photocurrent at Monochromatic Excitation of Superlattice and Responsivity of Superlattice Detector The exact solution of Boltzmann equation for arbitrary time-dependent electric field, which is assumed homogenous inside the superlattice due to the smallness of superlattice sizes compared with wavelength in the THz range, at single v scattering frequency approximation, which is determined as follows:

$$f(p,t) = \int_{-\infty}^{t} v dt_1 \ \exp[-v(t-t_1)] f_o\left(p - \int_{t_1}^{t} eE(t_2) dt_2\right) \quad (1)$$

where $$f_o(p) = \frac{d}{2} \{\pi h_o(\Delta/2k_aT))^{-1}$$

$\exp[(\Delta/2k_BT)\cos(pd/h)]$ is the equilibrium distribution function, T is the lattice temperature, $I_o(x)$ is the modified Bessel function, $k_B$ is the Boltzmann constant; the energy spectrum is taken in the tight-binding approximation $$\epsilon(p) = (\Delta/2)[1-\cos(pd/h)], \quad (2)$$

where d is the superlattice period, $\Delta$ is the width of first allowed superlattice miniband, p is the electron momentum parallel to the direction of superlattice potential. From the equations (1–2) we obtain an expression for the drift current:

$$I(t) = 2I_p \int_{-\infty}^{t} v dt_1 \ \exp[-v(t-t_1)] \sin\left(\frac{e}{Nh}\int_{t_1}^{t} V(t_3) dt_3\right), \quad (3)$$

where V(t)=NdE(t) is the voltage applied to superlattice, $I_p = Sj_p = Sen\Delta d/(4 \ h)$ is the peak current of Esaki-T su I–V characteristic, S is the area of the superlattice contact, n is the electron concentration. We assume that electron mean free path $I_{FP} = \Delta d/(2 \ hv)$ is smaller than the superlattice length Nd in order to neglect the influence of the boundaries on the superlattice high-frequency properties.

We now suppose that in addition to the dc voltage $V_{dc}$, an alternating sinusoidal voltage with complex amplitude $V_\omega$ is applied to the superlattice:

$$V(t) = V_\infty + \frac{1}{2}[V_\infty \exp(i\omega t) + V_\infty^1 \exp(-i\omega t)]. \quad (4)$$

Let us assume that the external ac voltage $V_\omega$ is so small that perturbation theory holds, while the dc voltage $V_{dc}$ applied to superlattice keeps its finite value. Expanding the equation (3) around $V_{dc}$ at $V_\omega \to 0$ in a Taylor series, we obtain the time-dependent electric current flowing in the superlattice:

$$I(t) = I_\infty(V_\infty) + \frac{1}{2}[G_\infty(\omega, V_\infty)V_\infty \exp(i\omega t) + \quad (5)$$
$$cc.] + \Delta I_\infty(\omega, V_\infty),$$

where $G_{dc}(\omega,V_{dc})=G_o F_l(\omega,V_{dc})$ is the superlattice ac conductance. $^{11}G_{0=21P} IV_P$ is the superlattice conductance at $\omega \to 0$, $V_{dc} \to 0$, and $$F_1(\omega, V_\infty) = \frac{1 + i\omega t - (V_\infty/V_p)^2}{[1+(V_\infty/V_p)^2][(1+i\omega t)^2 + (V_\infty/V_p)^2]}, \quad (6)$$

is the dimension function which describes the dependence of the superlattice conductance both frequency and applied dc voltage, $\tau = v^{-1}$, $I_{dc}(V_{ac})$ is the Esaki-Tsu current-voltage characteristics:

$$I_\infty(V_\infty) = 2I_p \frac{(V_\infty/V_p)}{[1+(V_\infty/V_p)^2]},$$

where $V_p = NdE_p$ is the voltage, which corresponds to the maximum current. Further, the induced dc current change in the superlattice caused by absorbed THz photons is written as followng[11]

$$\Delta I_\infty(\omega, V_{ts}) = \frac{1}{4}|V_\infty|^2 F_2(\omega, V_\infty), \quad (7)$$

where $$F_2(\omega, V_\infty) = -\frac{4I_p}{V_p^2} \frac{(V_\infty/V_p)[3+(i\omega t)^2 - (V_\infty/V_p)^2]}{[1+(V_\infty/V_p)^2][1+} . \quad (8)$$
$$(V_\infty/V_p + i\omega t)^2][1+(V_\infty/V_p - i\omega t)^2]$$

The ac power $P_{abs}$ absorbed in the superlattice is found as following:

$$P_{sn} = \frac{1}{2} \text{Re} G_\infty(\omega, V_{ts})|V_\infty|^2. \quad (9)$$

Example 3

Lateral Superlattice as a Possible THz Detector

The lateral (surface) superlattice is a superlattice where an additional potential is produced for two dimensional electrons localized near a surface of semiconductor substrate. It can be the one-dimensional chains of identically coupled GaAs/GaAlAs quantum dots—a form of quantum wires, sometimes called quantum boxes, or quantum dots (GaAs) imbedded in a thin epilayer of GaAlAs.

The lateral superlattices are grown by means of Molecular Beam Epitaxy (MBE) and also by Metalorganic Chemical Vapor Deposition (MOCVD). Furthermore, the lateral superlattice can be successfully overgrown with upper substrate. The lateral superlattice is not necessarily a thin superlattice. At present, there has been a technological advance culminating in the growth of three-dimensional cluster lattice, what is actually a range of lateral superlattices grown one on another. The energy spectrum for the two-dimensional surface superlattice is more complicated than for the one-dimensional layered superlattice but it is assumed that the internal electric field in the lateral superlattice has only one non-zero component parallel to (one of) compositional potential direction(s), so the energy spectrum will always be given by the expression.

As compared to the design of the THz detector based on layered superlattice one can note that the main distinguishable part is the change in technology attachment of broadband THz antenna. Now both antenna tips lie on the same substrate, on which a lateral (surface) superlattice is also grown, being attached to superlattice through the Ohmic contacts. The substrate is the semi-insulating crystal, for example, undoped (intrinsic) GaAs. The lateral superlattice can be formed, as it is mentioned above, by quantum dots (GaAs) imbedded in a thin epilayer of GaAlAs (FIG. 8) or by quantum wires, but there is an obvious requirement that embedded quantum dots or quantum wire chains must lead to the appearance of miniband in the energy spectrum, or, in other words, a quantum superlattice must be formed. This is the principal detector design independent of scale. The sizes are arbitrary in some sense. The superlattice width (h) is usually from 0 to 1 micron and can be larger, and the length a or the contact between superlattice and antenna tip, can be varied to affect the responsivity value. The structure can be grown by MBE technology. In FIGS. 2 and 3 $P_i$ and $P_r$ are the incident and reflected wave powers, respectively. The external dc bias is applied through the Ohmic contacts.

The high-frequency electric field in the superlattice $E_\omega$ excited via broadband antenna is parallel to the antenna plane in comparison to its perpendicular direction (with respect to coplanar antenna tips) in the existent detector based on a layered superlattice.

Switching to lateral superlattice as the THz detector has several benefits. One of the benefits is better electron transport. The best value of the effective scattering frequency in the lateral superlattice is $f_{sc}^{min} \Delta 0.05$ THz[12] in comparison to such value in one-dimensional layered superlattice $f_{sc}^{min} \Delta 0.12$ THZ[22] at room temperature. This "plane" detector configuration allows creation of a resonant structure, and the high frequency current excited in the antenna and flowing through superlattice pumps a resonator.

Example 4

Resonant Detector Based on Lateral Superlattice

One possible design of the frequency-selective THz-photon detector is based on a lateral superlattice with a built-in resonator. The device uses a standing wave enhancement of the detector responsivity, which has been successfully realized in the optical band. The detector consists of a lateral superlattice overgrown with upper substrate, a broadband THz antenna, and a resonator formed by two metal mirrors. The conspicuous stratification of the structure allows its growth by MBE technology. The width L must satisfy the resonance condition $L=\lambda/2$ ($\lambda$ is the wavelength in the resonator infill $\lambda=c/f\epsilon_s^{1/2}$, $c=3\times10^8$ ms$^{-1}$, $\epsilon_s$ is the terahertz infill permittivity), for some frequency $f_0$, near which a responsivity enhancement is noted. The effect of a resonant enhancement will be achieved in such detector near this frequency only under the condition that the Q-factor of this resonator is high, which is possible if the characteristic sizes of the metal mirrors are comparable with $\lambda$. FIGS. 1–8 are representative of the basic configurations of the resonant detector of the present invention, however, there are numerous possible modifications. For example, the lower (lower with respect to the illuminated antenna surface) mirror is not necessary if the size a is comparable with $\lambda$. At that, the resonator will be formed by the upper mirror and antenna plane. Removal of the upper mirror would be completely wrong even if $a=\lambda$ because of the skin-effect physics: the high-frequency current excited in antenna is localized near the illuminated antenna surface with a deep of skin-layer and cannot efficiently pump the lower resonator.

As it is clearly understood from this resonant design, it is not necessarily only for terahertz range, and, secondly, not necessarily with a lateral superlattice as an active material. Any active material in the corresponding microwave or terahertz range can be applied. There is only one condition, namely, that the nonlinear medium must be a lateral (or surface) structure.

Example 5

Responsivity of the Resonant Detector

The frequency dependence of the responsivity of the proposed frequency-selective detector is based upon a lateral superlattice with built-in resonator.

It is clear that such a description is approximate for the present detector, first of all, because of the mentioned above skin-effect in the antenna plane, and, secondly, it neglects the diffraction corrections for the electromagnetic field distribution inside the resonator. This transmission line correctly describes the structure when the size a is much smaller than $\lambda$. The system of equations for all propagating waves, which exist in the structure, taken at the lateral superlattice position $0=x$ is the following:

$$V_i+V_r=V_iV_i=V_iV_i=V_i$$

$$V_i \exp(ikL)V_i \exp(ikL)=V_i \exp(ikL)+V_i \exp(ikL)=0$$

$$V_i+V_rV_i+V_r-V_i+V_r=V_i+V_r$$

$$Z_A Z_W Z_W Z_C$$

where $V_i$, 1 $V_i$, 2 $V_i$, $V_r$, 1 $V_r$, 2 $V_r$ are the voltage amplitudes of all six waves in the structure.

What is claimed is:

1. A device for frequency-selective detecting electromagnetic radiation in the terahertz region of the electromagnetic spectrum comprising:
   (a) a lateral semiconductor superlattice;
   (b) a metal antenna attached to said lateral semiconductor superlattice; and
   (c) a built in photon resonator installed to a selected frequency comprising two metal mirrors comprising a bulk medium, metal powder or n+ (n++) doped semiconductor layer and a substrate, so that the first and second metal mirrors are arranged parallel to the plane of the bowtie antenna and lateral semiconductor superlattice axis for power cumulation and frequency filtering of incident radiation on the lateral semiconductor superlattice, wherein the metal antenna connects the lateral semiconductor superlattice to an external circuit with a voltage source that allows a current to flow through the lateral semiconductor superlattice so that the effect of incident radiation absorption within one miniband in the lateral semiconductor superlatiice induces an additional current flowing in an external circuit which can be readily detected.

* * * * *